(12) United States Patent
Paponneau et al.

(10) Patent No.: US 7,156,874 B2
(45) Date of Patent: Jan. 2, 2007

(54) SPINAL INTERVERTEBRAL IMPLANT ADJUSTABLE IN SITU COMPRISING HARD PASS POINT

(75) Inventors: Francois Paponneau, Gradignan (FR); Frédéric Conchy, Saint-Médard d'Eyrans (FR)

(73) Assignee: Stryker Spine (FR)

( * ) Notice: Subject to any disclaimer, the term of this patent is extended or adjusted under 35 U.S.C. 154(b) by 167 days.

(21) Appl. No.: 10/433,769

(22) PCT Filed: Dec. 5, 2001

(86) PCT No.: PCT/FR01/03838

§ 371 (c)(1),
(2), (4) Date: Apr. 30, 2004

(87) PCT Pub. No.: WO02/45625

PCT Pub. Date: Jun. 13, 2002

(65) Prior Publication Data

US 2005/0209697 A1    Sep. 22, 2005

(30) Foreign Application Priority Data

Dec. 5, 2000    (FR) ................... 00/15736

(51) Int. Cl.
*A61F 2/44* (2006.01)

(52) U.S. Cl. .................................. 623/17.11

(58) Field of Classification Search ............. 623/17.11, 623/17.16, 17.12
See application file for complete search history.

(56) References Cited

U.S. PATENT DOCUMENTS

| | | | |
|---|---|---|---|
| 5,702,453 A | * | 12/1997 | Rabbe et al. ............. 623/17.16 |
| 5,702,455 A | | 12/1997 | Saggar |
| 5,916,267 A | | 6/1999 | Tienboon |
| 5,989,290 A | * | 11/1999 | Biedermann et al. .... 623/17.11 |

FOREIGN PATENT DOCUMENTS

| | | |
|---|---|---|
| DE | 196 22 827 | 12/1997 |
| EP | 0 567 424 | 10/1993 |
| WO | WO-99 56675 | 11/1999 |

OTHER PUBLICATIONS

International Search Report completed on Mar. 18, 2002.

* cited by examiner

*Primary Examiner*—Eduardo C. Robert
*Assistant Examiner*—David Comstock
(74) *Attorney, Agent, or Firm*—Lerner, David, Littenberg, Krumholz & Mentlik, LLP (57) ABSTRACT

The invention concerns a spinal intervertebral implant (200) comprising at least an upper element (203), a lower element (205), and an intermediate member (201) adapted to co-operate with the upper and lower elements by helical linking means (207, 254) including means (216) forming hard pass points when the helical linkage is carried out.

24 Claims, 7 Drawing Sheets

FIG_1

FIG. 2

FIG_3

FIG_4

FIG. 7

SPINAL INTERVERTEBRAL IMPLANT ADJUSTABLE IN SITU COMPRISING HARD PASS POINT

The invention concerns implants of the intervertebral cage type, or of the type for replacement of vertebral bodies, intended for the spinal column.

The document WO 99/56675 discloses an implant intended for the replacement of vertebral bodies and comprising a first, central element with two threads, the pitches of which threads run counter to one another. It also comprises two end elements, that is an upper end element and a lower end element, which can be screwed onto said central element. In this way, the implant can be adjusted in situ by rotating the central element. Thus, the two end elements, that is the upper end element and the lower end element, are moved away from one another or closer to one another depending on the sense of rotation of the central element. However, in the case of this maneuver, it is difficult to know how the adjustment stands. This entails a maneuvering difficulty in surgical operations, the result being a prolongation of the operating time.

It is an object of the invention to make available an implant of the intervertebral cage type, or of the type for replacement of vertebral bodies, which it is possible to adjust in situ in a sufficiently quick and precise manner.

For this purpose, provision is made, according to the invention, for a spinal intervertebral implant comprising at least an upper element, a lower element, and an intermediate member which can cooperate with the upper and lower elements via helical linking means which include means forming hard pass points when the helical linkage is carried out.

Thus, the means forming hard pass points permit indexing of the in situ adjustment in a simple and precise manner for the surgeon.

Advantageously, the screwing means comprise at least a helical cam and a cam follower which can come into contact with a bearing surface of the cam.

Advantageously, the bearing surface has zones forming the hard pass points.

Advantageously, the zones forming the hard pass points comprise pass points protruding from the bearing surface.

Advantageously, the upper pass points are bosses.

Advantageously, the intermediate member comprises the cam.

Advantageously, the intermediate member comprises the cam follower.

Advantageously, the intermediate member can be received in one of the upper and lower elements.

Advantageously, the intermediate member can be received in the other of the upper and lower elements.

Advantageously, one of the upper and lower elements can be received in the intermediate member.

Advantageously, the other of the upper and lower elements can be received in the intermediate member.

Advantageously, the helical linkage between the intermediate member and the upper element has a direction of screwing counter to that of the helical linkage between the central element and the lower element.

Advantageously, the implant additionally comprises means for blocking in position at least one of the upper and lower elements relative to the intermediate member.

Advantageously, the means for blocking in position comprise at least one stud.

Advantageously, the stud comprises a part which is eccentric in relation to the main axis of use of the stud.

Advantageously, the stud comprises a part which can be screwed.

Advantageously, the implant comprises means for anchoring the implant in vertebral plateaus.

Advantageously, the upper and lower elements can fit into one another through being of complementary shape.

Advantageously, the upper and lower elements fit into one another with sliding.

Advantageously, each upper and lower element has a general U-shape, the elements being able to fit into one another with the U-shapes in opposition.

Advantageously, with at least one of the upper and lower elements comprising the cam, said cam has an opening opposite its bearing surface.

Provision is also made, according to the invention, for a surgical method which comprises the steps of positioning the implant at the implantation site and adjusting said implant in situ by using the screwing means between the central element and the end elements, the screwing means having means which form hard pass points.

Advantageously, the surgical method additionally comprises a step of filling the implant with a substance that promotes bone growth.

Other characteristics and advantages of the invention will become evident from the following description of a preferred embodiment of the invention and of an alternative embodiment given as nonlimiting examples. In the attached drawings.

A first embodiment of the invention will be described with reference to FIGS. 1 through 4. The implant 400 of the intervertebral cage type in this present embodiment comprises the following main elements: an upper base 403, a lower base 407, and an intermediate element 401 which can be received with sliding and rotation inside the upper and lower bases.

Figure 4:
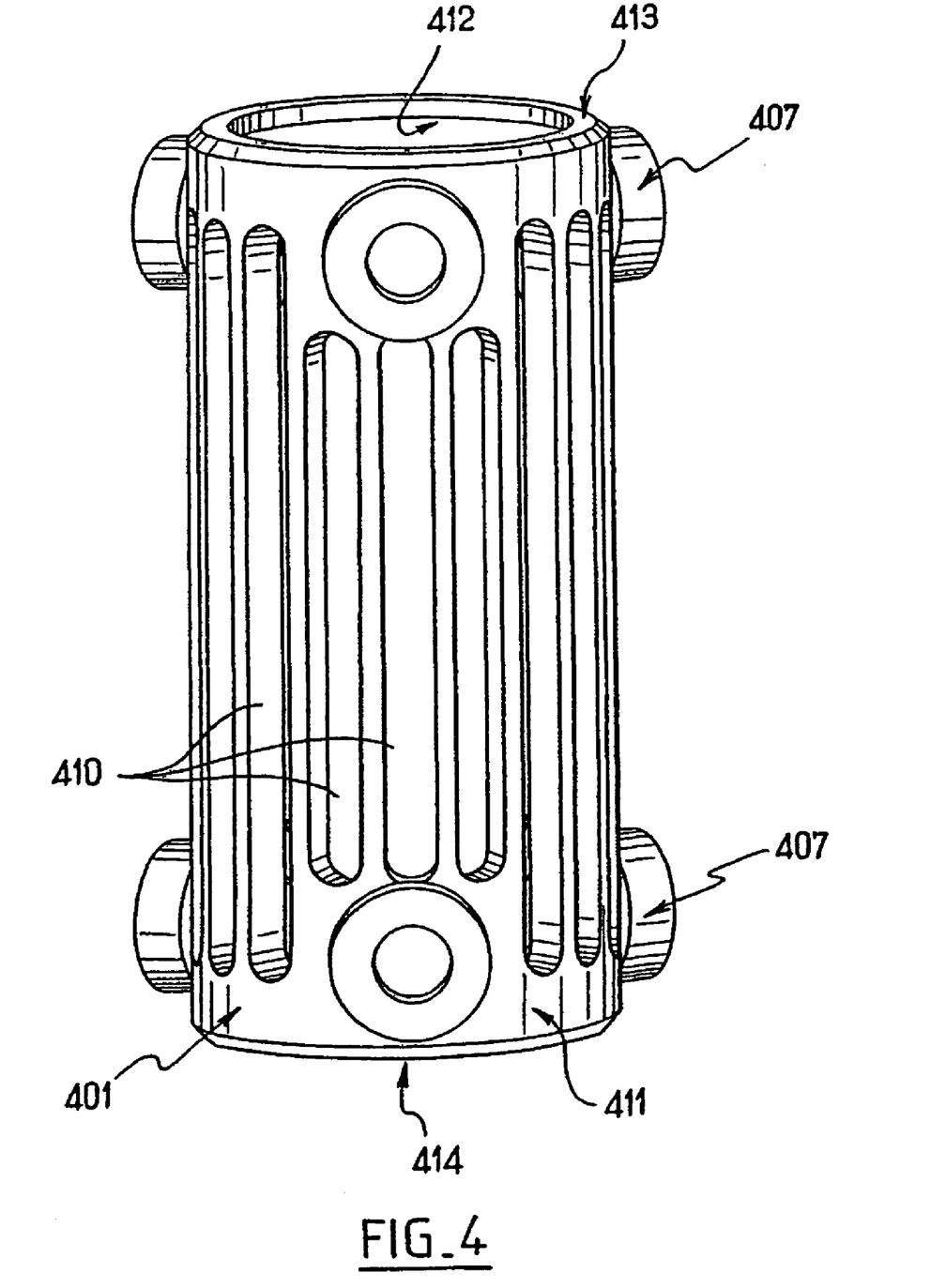
FIG. 4 is a view, in three dimensions, of the intermediate element of the first embodiment from FIG. 1.

The intermediate element 401 is a tube having an internal diameter and an external diameter. The wall of the tube comprises a plurality of longitudinal openings 410 similar to elongate slots. These openings 410 have their main dimension parallel to a generatix of the tube forming the intermediate element and are parallel to one another. The openings 410 extend radially from the outer face 411 to the inner face 412, these faces delimiting the thickness of the tube forming the intermediate element 401. This intermediate element 401 thus has an internal hollow space which extends from an upper face 413 to a lower face 414 and which is delimited radially by the inner face 412. The internal hollow space can receive any osteoconductive or osteoinductive substance that promotes bone fusion.

Moreover, the intermediate element 401 comprises a plurality of studs 407 protruding outward in a radial direction from the outer face 411 of the intermediate element 401. The studs 407 are uniformly distributed about the circumference of the tube in two groups situated, respectively, near the upper end face 413 and lower end face 414. Each group here comprises three studs 407. Each of the studs 407 has what is called a contact surface 474, a plane front face 472 perpendicular to the surface 474, and engagement means 470. The surface 474 is a surface of revolution, here cylindrical, while the face 472 is plane and circular. The height of the studs 407 is such that, once the implant 400 has been mounted, the face 472 is flush with the outer face 473 of the bases 403 and 405, which bases will now be described.

Figure 3:
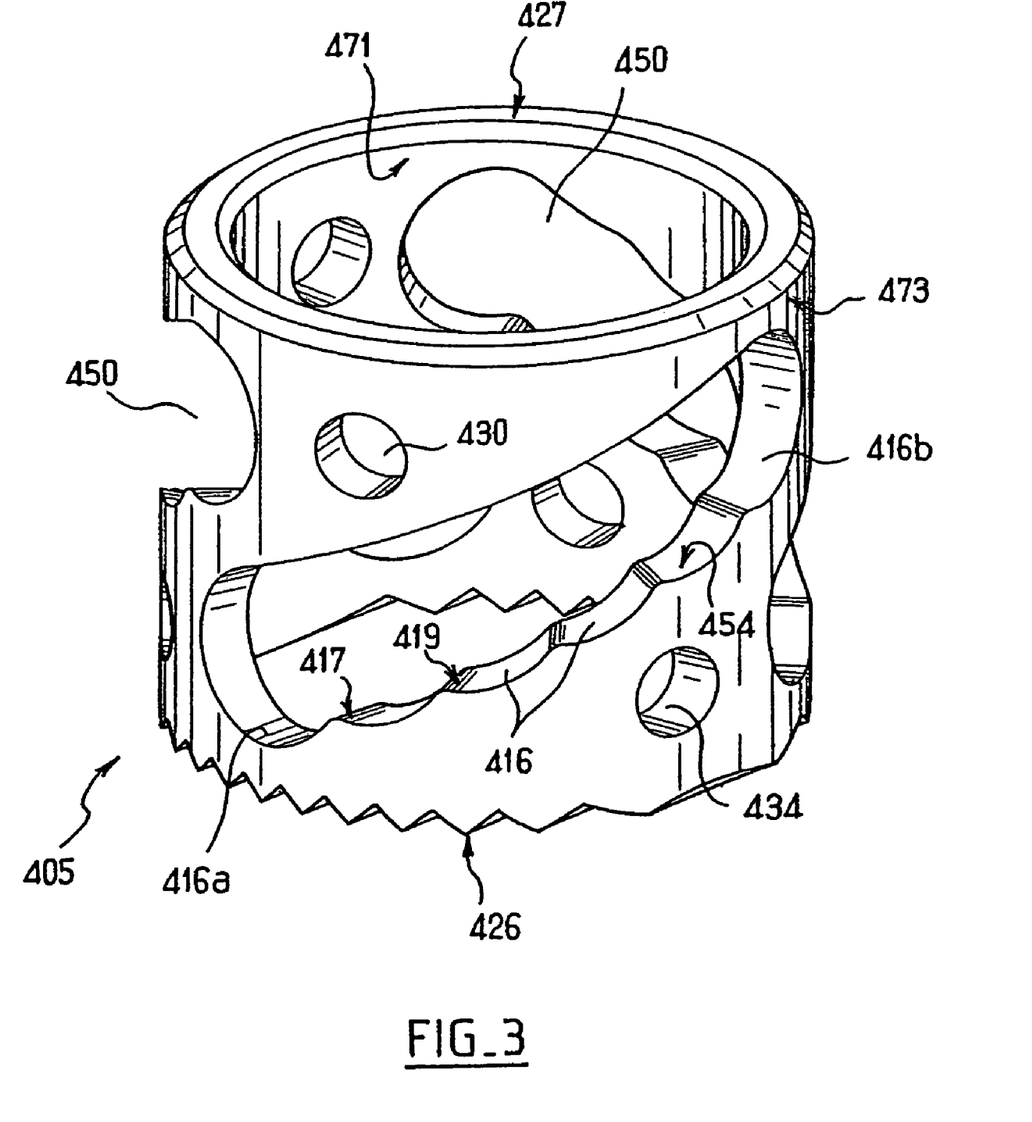
FIG. 3 is a view, in three dimensions, of one of the bases of the first embodiment from FIG. 1.

Referring to FIG. 3, the lower base 405 is, here, a tube having an upper face 427, a lower face 426, an outer face 473, and an inner face 471. The internal diameter of the tube is substantially equivalent to the external diameter of that forming the intermediate element 401. Thus, upon assembly of the implant 400, the face 471 is in contact with the face 411, and the intermediate element 401 is mounted movably with sliding and rotation on the base 405. The upper face 427 is perpendicular to the axis of revolution of the tube forming the base 405. The lower face 426, here substantially parallel to the face 427, comprises a plurality of teeth 422, here profiled with a triangular section and parallel to one another. The teeth 422 in the present case form means of anchoring in the vertebral plateaus with which the face 426 can come into contact.

The outer face 473 comprises a plurality of openings 450 of helical form which extend through the thickness of the wall of the tube forming the base 405 and which are uniformly distributed about the circumference of the base 405. Here, they are three in number. Each opening 450 has a smooth face 452 situated toward the plane face 472 of the base 405 and forming a single ramp. The opening 450 additionally has an opposite surface 454, facing and substantially parallel to the face 452. This surface 454, called a contact surface, comprises a group of several ramps 416, here six in number, of concave form, whose radius of curvature is substantially equal to the radius of the surface 474 of the studs 407 with which the ramps 416 can come into contact during use of the implant 400. Each ramp 416 comprises a low end 417 and a high end 419. The arrangement of the ramps 416 within the group is such that a high end of one ramp forms the low end of the following ramp. The ramps 416*a* and 416*b*, called end ramps, of the group do not have a low end or high end, respectively, because their surface continues with the same radius of curvature in such a way as to tangentially rejoin the face 452 and thus complete the opening 450.

Moreover, the outer face 473 of the base 405 comprises a plurality of orifices 430 of circular cross section which are threaded (the thread is not shown), are situated near the face 427, are uniformly distributed about the circumference of the base 405, and are able to receive a lock 432 which is screwed in. The lock is longer than the thickness of the wall of the base 405 so as to be able to engage in one of the openings 410 of the intermediate element 401. The role of the lock 432 is to secure the assembly of the implant 400, as will be seen later in the description.

Figure 8:
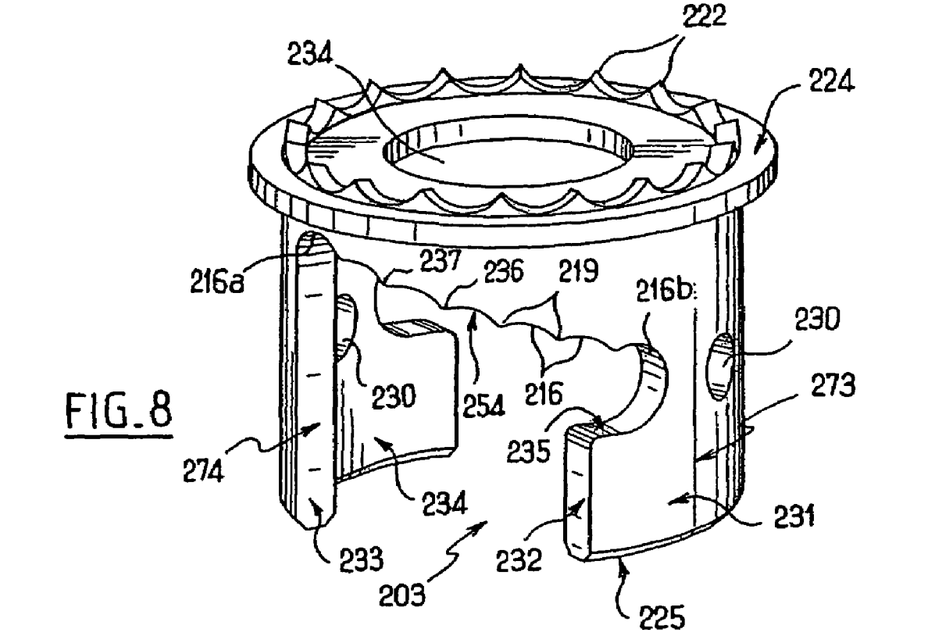
FIG. 8 is a view, in three dimensions, of one of the bases of the second embodiment from FIG. 5.

Similarly, the outer face 473 of the base 405 comprises a plurality of orifices 434 of circular cross section which are smooth, are situated near the face 426 of the base 405, and are uniformly distributed about the circumference of the base 405. These orifices are able to improve the communication between the outside and the inside of the implant 400 when the latter is in the high configuration, as is illustrated in FIG. 8.

Figure 1:
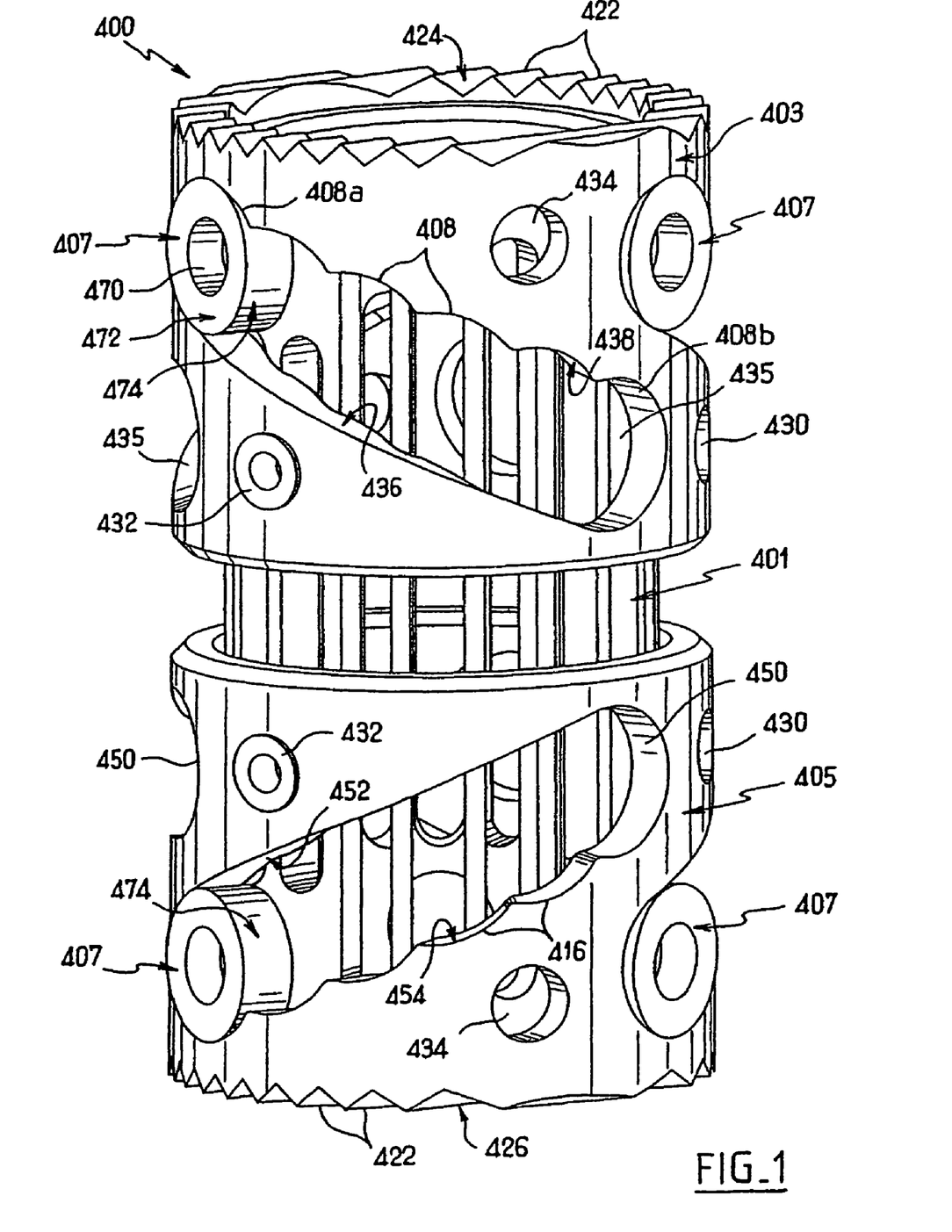
FIG. 1 is a view, in three dimensions, of a first embodiment of the invention in the position of minimum height.
Figure 2:
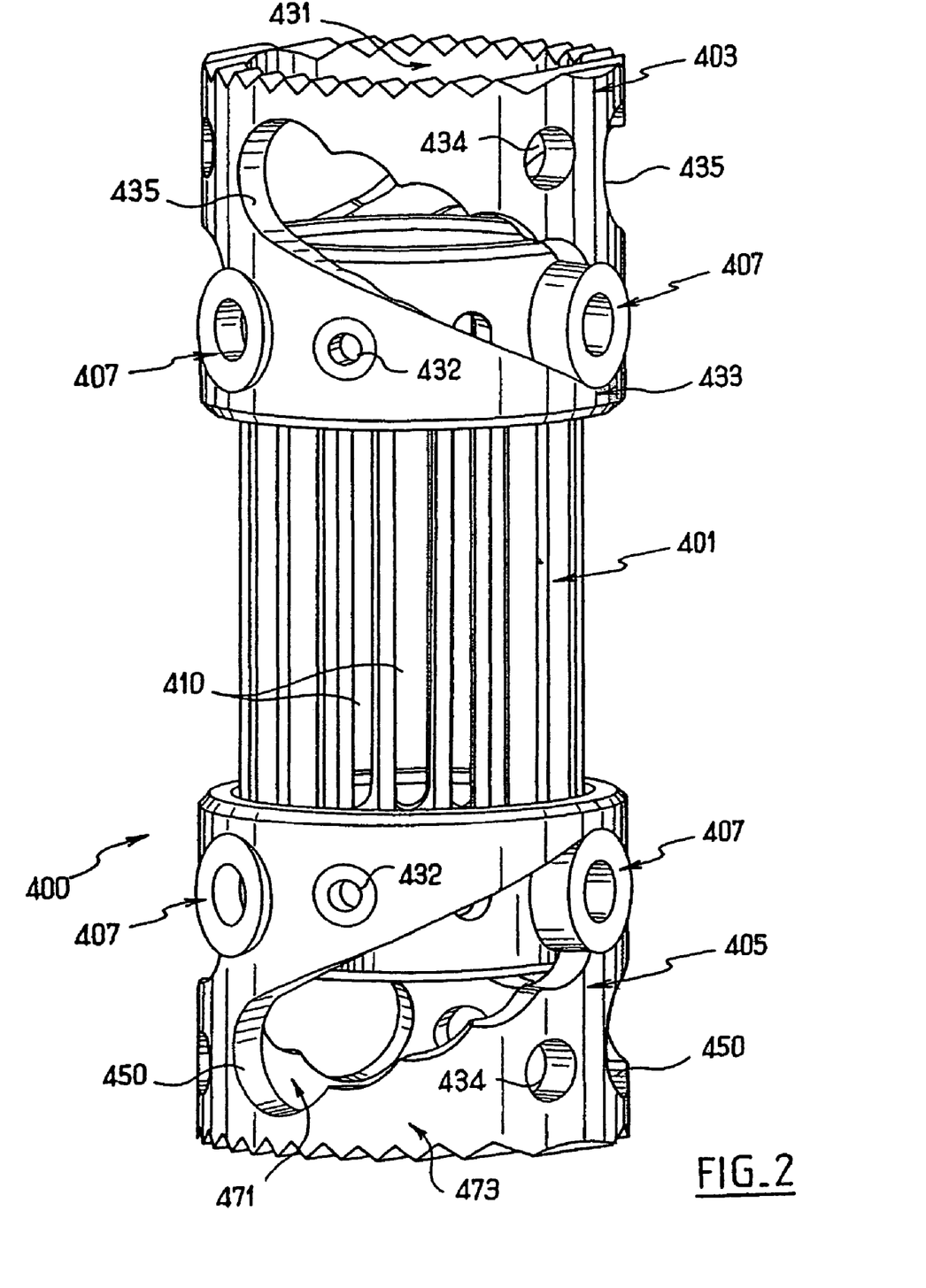
FIG. 2 is a view, in three dimensions, of the first embodiment of the invention in the position of maximum height.

The upper base 403 is, in a transverse plane perpendicular to the axis of revolution of the base, the mirror-symmetrical counterpart of the lower base 405 which has just been described in detail. The base 403 comprises a plurality of openings 435 symmetrical to the openings 450: each opening 435 comprises a smooth face 436 forming a single ramp, a surface 438, called the contact surface, opposite the face 436 and comprising a group of a plurality of ramps 408 similar to the ramps 416. The group comprises ramps 408*a* and 408*b*, called end ramps, whose surface continues in the same radius of curvature in order to tangentially rejoin the face 436. The base 403 additionally comprises a face 424 with anchoring means 422, here teeth similar to those present on the face 426 and previously described.

At the time of the surgical intervention, the surgeon establishes the access route and then prepares the implantation site. He then assembles the implant 400 by choosing the intermediate element 401 and also a base 403 and a base 405. He joins the bases to the intermediate element. He places the various studs 407 on the element 401 via the helical openings 435 and 450. He fills the inside of an implant 400, thus formed, with an osteoinductive or osteoconductive substance. He then places the implant 400 in the implantation site. He adjusts the height of the implant 400 by turning the intermediate element 401, while the bases 403 and 405 are immobile because of the anchoring means impacted into the vertebral plateaus delimiting the implantation site. Rotation of the implant 401, on account of the helical linkage joining the intermediate element 401 to each base 403, 405, causes the studs 407 to move in their respective openings 435 and 450, their surface 474 passing from one ramp 416, 408 to another, thus permitting adjustment of the height of the implant. Once the desired distraction height has been obtained, the surgeon secures the implant 400 in the distraction position, by using the position-blocking means 432, then closes his access route. By virtue of the discontinuities between the ramps 416, the surgeon knows that each ramp passage corresponds to a fixed increase or decrease in height. This indexing of the height adjustment means that the surgeon knows how the distraction of the implantation site stands.

A second embodiment of the invention will be described with reference to FIGS. 5 through 9. The implant 200 of the intervertebral cage type in this embodiment comprises three main elements: an upper base 203, a lower base 205, and an intermediate element 201. The upper 203 and lower 205 bases can be received with sliding and rotation inside the intermediate element 201 in order to form a helical linkage as in the aforementioned first embodiment.

Figure 7:
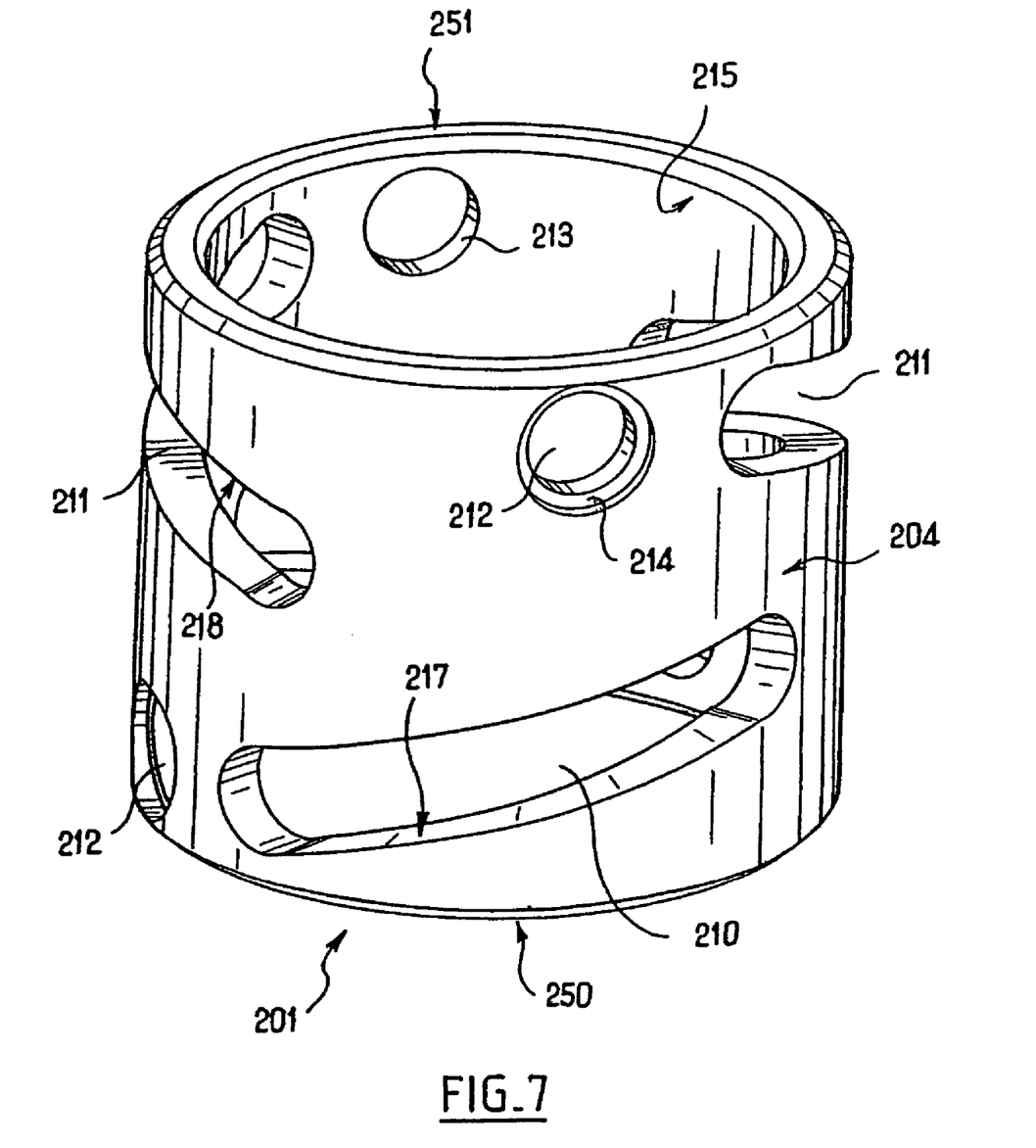
FIG. 7 is a view, in three dimensions, of the intermediate element of the second embodiment from FIG. 5.

The intermediate element 201 is a tube having an internal diameter and an external diameter. The wall of the tube comprises a first plurality of openings 210, of helical form, whose helix is screwed in the direction of rotation of the hands of a clock, downward when its axis is vertical. These openings 210, here numbering two, are uniformly distributed about the circumference of the tube and are situated near the lower end face 250. Likewise, the wall of the tube comprises a second series of helical openings 211 whose helix is screwed in the opposite direction to the hands of a clock, downward when its axis is vertical. These openings 211, here also numbering two, are uniformly distributed along the circumference of the tube and are situated near the upper end face 251. The openings 210 and 211 each have a bearing surface 217, 218, respectively. The bearing surfaces can come into contact with position-blocking means (not shown in the figures), as will be seen later in the description.

Moreover, near the upper 251 and lower 250 end faces, the intermediate element 201 comprises a plurality of circular orifices 212 uniformly distributed about the circumference of the tube and here numbering two. These orifices 212 extend through from the outer face 204 to the inner face 215. Each of the orifices 212 comprises a threaded part 213 and a countersink 214 whose diameter is greater than that of the threaded part 213. The thread 213 can cooperate with the thread present on a stud 207, which will be described below. Likewise, the countersink 214 can receive the head of the stud 207.

Each of the studs 207 comprises a substantially plane and circular face 272 in which engagement means 270 are formed, here in the form of a hexagonal socket. Once in place, the stud 207 is flush with the outer face 204 of the intermediate element 201. Moreover, the length of this stud 207 is much greater than the thickness of the tube forming the intermediate element. This is so that it can come into contact with a part 254 of the upper 203 and lower 205 bases, as will now be described.

Referring to FIG. 8, only the upper base 203 will be described, because the lower base 205, in a transverse plane perpendicular to the axis of revolution of the base, is the mirror-symmetrical counterpart of the upper base 203 which will now be described in detail. The upper base 203 is, here, a tube having an upper face 224, a lower face 225, an outer face 231, and an inner face 234. The external diameter of the tube is substantially equivalent to the internal diameter of that forming the intermediate element 201. Thus, upon assembly of the implant 200, the face 231 is in contact with the face 215, and the upper base 203 is thus mounted movably with sliding and rotation in the intermediate element 201. The lower face 225 is perpendicular to the axis of revolution of the tube forming the base 203. The upper face 224, here substantially parallel to the face 225, comprises a plurality of teeth 222, here profiled with a triangular cross section having concave sides and uniformly distributed in a circle having, as its center, the axis of revolution of the tube forming the base 203, and having a diameter corresponding to the mean of the internal and external diameters of said tube forming said base 203. The teeth 222 in the present case form means of anchoring in the vertebral plateaus with which the face 224 will come into contact. Moreover, the face 224 has a circular orifice 234 with its center the axis of revolution of the tube forming the base 223.

The body of the base comprises two extensions forming branches 273 and 274. These two extensions are symmetrical to one another, on the axis of revolution of the tube forming the base 203. The two extensions 273 and 274 delimit, on either side of the axis, two openings which are each open toward the lower 225 end face of the base 203, said openings comprising a first substantially vertical lateral face 233, an upper face 254, a face 235, and a second substantially vertical lateral face 232 which is substantially parallel to the first lateral face 233. The upper face 254 called the contact surface or bearing surface comprises a group of several ramps 216, here seven in number, of concave shape whose radius of curvature is substantially equal to the radius of that part of the studs 207 with which the face 254 can come into contact upon use of the implant 200. Each ramp 216 comprises a low end 236 and a high end 237. The arrangement of the ramps 216 within the group is such that the high end of one ramp forms the low end of the following ramp; the ramps 216a and 216b, called end ramps, of the group do not have a high end or low end, respectively, because their surface continues with the same radius of curvature so as to tangentially rejoin the face 233 and the face 235, respectively. The high and low ends 237, 236 form a plurality of bosses 219.

Moreover, the branch 273, like the branch 274 too, comprises a radially extending through-orifice 230 of circular cross section. This orifice 230 can receive the position-blocking means (not shown in the figures) of the implant 200.

Figure 9:
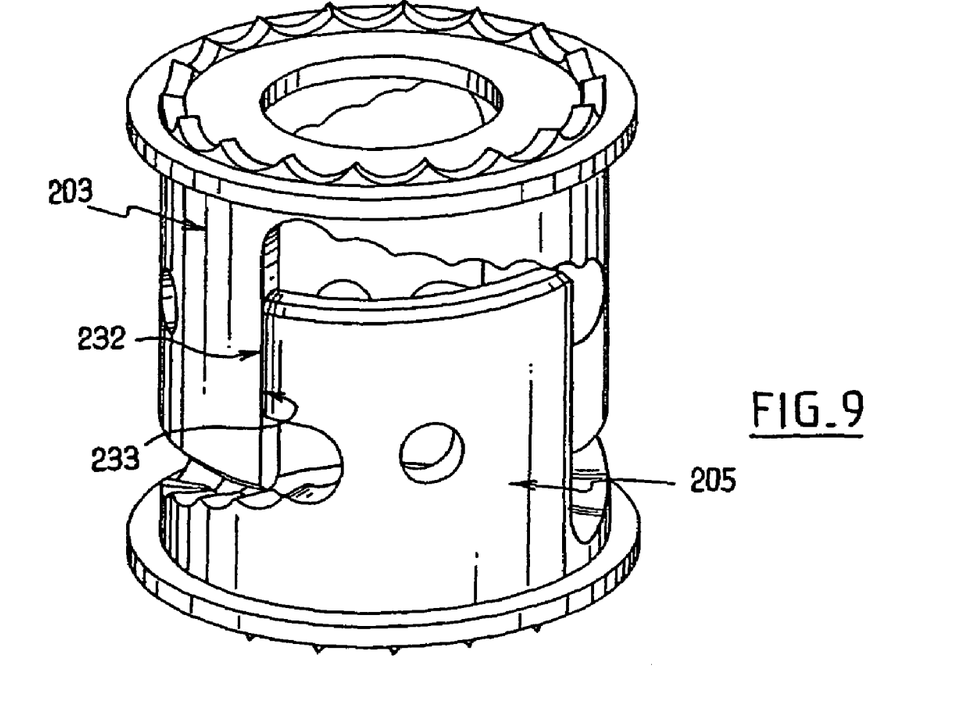
FIG. 9 is a view, in three dimensions, showing the arrangement of the two base elements of the second embodiment from FIG. 5.

Such an arrangement of the branches 273 and 274 of the base 203, and of their counterparts on the base 205 which is mirror-symmetrical to the base 203, as has been indicated above, allows the two bases to be fitted into one another upon assembly and use of the implant, as is illustrated in FIG. 9. The two bases 203 and 205 are mounted with sliding relative to one another, the different faces 232 of one of the bases being able to come into contact with the different faces 233 of the other base, respectively. During this fitting together, each extension penetrates into one of the openings.

Figure 5:
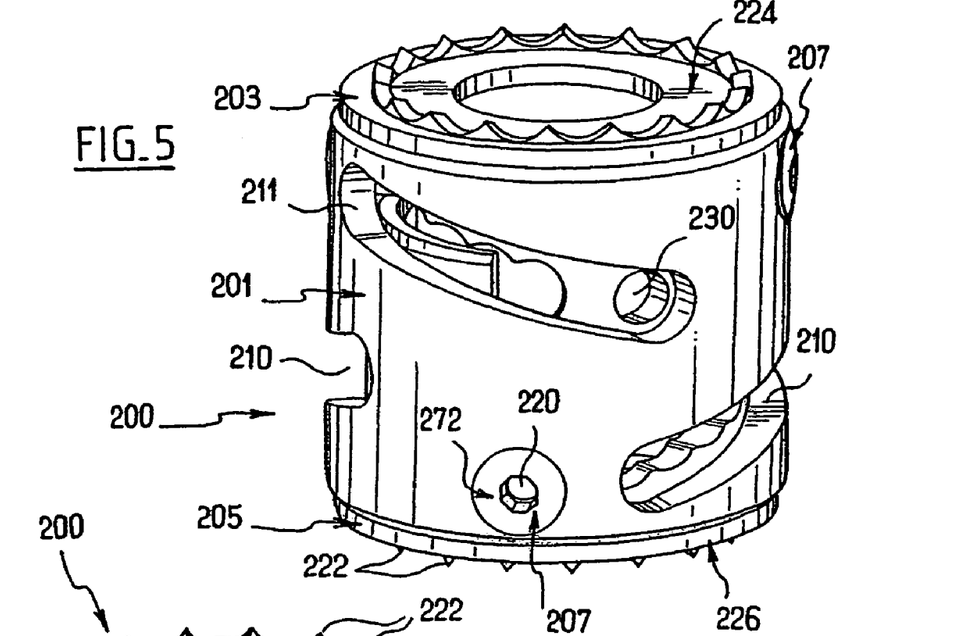
FIG. 5 is a view, in three dimensions, of a second embodiment of the invention in the position of minimum height.
Figure 6:
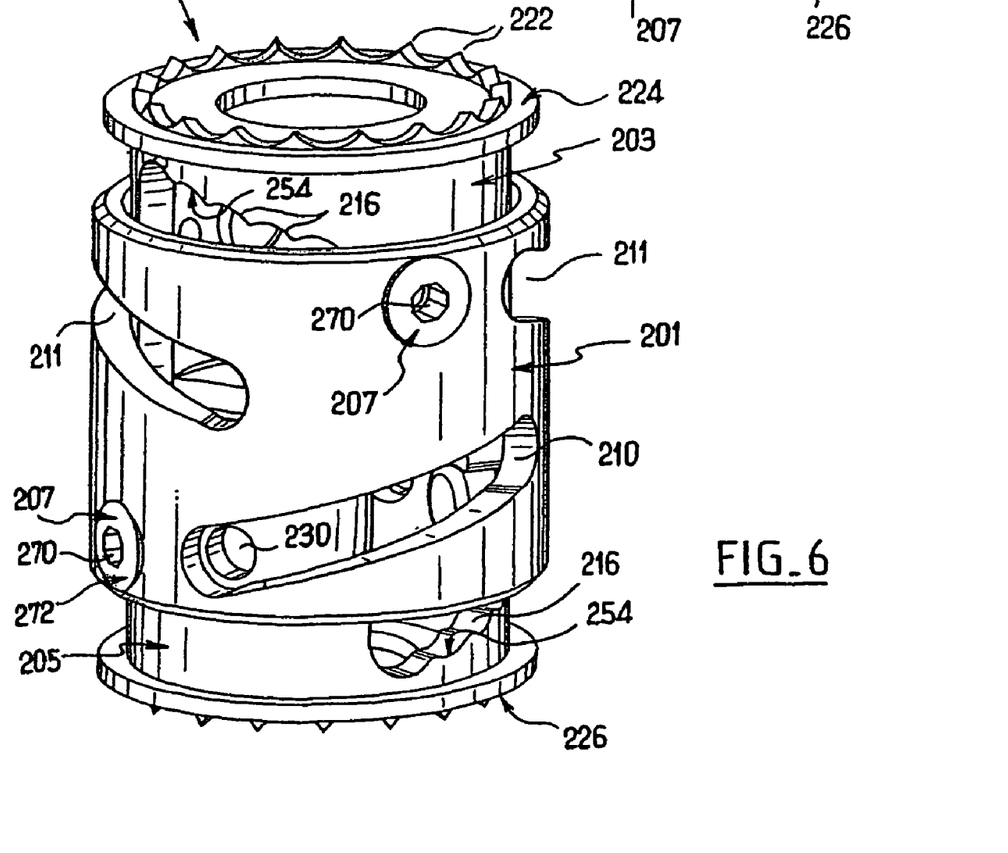
FIG. 6 is a view, in three dimensions, of the second embodiment of the invention in the position of maximum height.

At the time of the surgical intervention, the surgeon, as before, establishes the access route and then prepares the implantation site. He then assembles the implant 200 by choosing an intermediate element 201 and also a base 203 and a base 205. With the different studs 207 already in place on the intermediate element 201, in the orifices 212, he positions the two bases by inserting them inside the intermediate element 201, as is illustrated in FIG. 5, the studs 207 being in contact with the ramps 216a of the upper base 203 and of its symmetrical counterpart of the base 205. The implant is now in its lower configuration. He then fits the position-blocking means (not shown) through the slots 211 and 210, respectively, in the orifices 230 of the bases 203 and 205. The position-blocking means can be studs having a thread cooperating with a thread formed in the orifice 230, or studs which can be fitted with rotation in the orifice 230 and whose head received in the slots 210, 211 is eccentric in relation to the axis of the orifice 230. Once the implant 200 has been assembled, the surgeon fills the inside of the implant with an osteoinductive or osteoconductive substance. He then places the implant 200 in the implantation site. Then he adjusts the height of the implant by turning the intermediate element 201 while the bases 203 and 205 are immobile relative to the respective vertebrae, on account of the anchoring means impacted into the vertebral plateaus which delimit the implantation site. Rotating the intermediate element 201 causes the studs 207 to move along the ramps 216 of each of the openings in the bases 203 and 205. The surgeon then uses the position-blocking means, received through the slots 210 and 211, in order to block the implant in position. The surgeon then closes the access route.

It is of course possible for numerous modifications to be made to the present invention without departing from the scope of the latter.

The faces comprising the anchoring means could be inclined relative to a main perpendicular plane of the implant.

It is possible to conceive of any cam system with cam follower other than that described above, without departing from the present invention.

It could also be possible to provide an implant having upper and lower elements able to fit into one another through being of complementary form, for example as is illustrated in FIG. 9, without having helical linkages between the intermediate member and the upper and lower elements with means forming hard pass points.

The invention claimed is:

1. A spinal intervertebral implant comprising at least an upper element, a lower element, and an intermediate member which can cooperate with the upper and lower elements via helical linking means, wherein the helical linking means include cam and a cam follower which is able to come into contact with a bearing surface of the cam for forming hard pass points when the helical linkage is carried out, the intermediate member including the cam or cam follower.

2. The implant as claimed in claim 1, wherein the bearing surface has zones forming the hard pass points.

3. The implant as claimed in claim 2, wherein the zones forming the hard pass points comprise pass points protruding from the bearing surface.

4. The implant as claimed in claim 3, wherein the hard pass points are bosses.

5. The implant as claimed in claim 1, wherein the intermediate member can be received in one of the upper and lower elements.

6. The implant as claimed in claim 5, wherein the intermediate element can be received in the other of the upper and lower elements.

7. The implant as claimed in claim 1, wherein one of the upper and lower elements can be received in the intermediate member.

8. The implant as claimed in claim 7, characterized in that the other of the upper and lower elements can be received in the intermediate member.

9. The implant as claimed in claim 1, wherein the helical linkage between the intermediate member and the upper element has a direction of screwing counter to that of the helical linkage between the central element and the lower element.

10. The implant as claimed in claim 1, further comprising means for blocking in position at least one of the upper and lower elements relative to the intermediate member.

11. The implant as claimed in claim 10, wherein the means for blocking in position comprise a stud.

12. The implant as claimed in claim 11, wherein the stud comprises a part which is eccentric in relation to the main axis of use of the stud.

13. The implant as claimed in claim 11, wherein the stud comprises a part which can be screwed.

14. The implant as claimed in claim 1, further comprising means for anchoring the implant in the vertebral plateaus.

15. The implant as claimed in claim 1, wherein the upper and lower elements can fit into one another through being of complementary shape.

16. The implant as claimed in claim 15, wherein the upper and lower elements fit into one another with sliding.

17. The implant as claimed in claim 15 or 16, wherein each lower and upper element has a general U-shape, the elements being able to fit into one another with the U-shapes in opposition.

18. The implant as claimed in claim 15 or 17, wherein with at least one of the upper and lower elements comprising the cam, said cam has an opening facing its bearing surface.

19. A spinal intervertebral implant comprising:
    an upper element having a first slot which extends at an angle with respect to the longitudinal axis of said implant, said first slot having a plurality of first ramps along a length thereof;
    a lower element having a second slot which extends at an angle with respect to the longitudinal axis of said implant, said second slot having a plurality of second ramps along a length thereof; and
    an intermediate member having at least two studs disposed within the first and second slots of the upper and lower elements, whereby said studs are adapted to cooperate with said first and second ramps.

20. The implant of claim 19, wherein upon rotation of said upper and lower elements with respect to said intermediate member, the engagement between said studs and said ramps form hard pass points corresponding to different heights of said implant.

21. The implant of claim 20, further including set screws for locking said upper and lower elements with said intermediate member upon achievement of a desired implant height.

22. The implant of claim 21, wherein said upper and lower elements each include two slots having a plurality of ramps along their lengths, and said intermediate member includes four studs for cooperation with each said slot.

23. The implant of claim 20, wherein opposite rotation of said upper and lower elements with said intermediate member varies the height of said implant.

24. A spinal intervertebral implant comprising at least an upper element, a lower element, an intermediate member which can cooperate with the upper and lower elements via helical linking means and means for anchoring the implant in vertebral bodies, wherein the helical linking means include means for forming hard pass points when the helical linkage is carried out.

* * * * *

UNITED STATES PATENT AND TRADEMARK OFFICE
CERTIFICATE OF CORRECTION

| | | |
|---|---|---|
| PATENT NO. | : 7,156,874 B2 | Page 1 of 1 |
| APPLICATION NO. | : 10/433769 | |
| DATED | : January 2, 2007 | |
| INVENTOR(S) | : Francois Paponneau and Frédéric Conchy | |

It is certified that error appears in the above-identified patent and that said Letters Patent is hereby corrected as shown below:

Column 7, line 8, "include cam" should read --include a cam--.
Column 8, line 7, "17" should read --16--.

Signed and Sealed this

First Day of May, 2007

JON W. DUDAS
*Director of the United States Patent and Trademark Office*